US007468191B2

(12) United States Patent
Hsu et al.

(10) Patent No.: US 7,468,191 B2
(45) Date of Patent: *Dec. 23, 2008

(54) METHOD OF PREPARING GAS DELIVERING PERFLUOROCARBON EMULSIONS WITH NON-FLUORINATED SURFACTANTS

(75) Inventors: Li-Chien Hsu, Mission Viejo, CA (US); Jeffrey L. Creech, Marina Del Rey, CA (US); Paul J. Zalesky, Newport Beach, CA (US); Margaret A. Kivinski, Laguna Niguel, CA (US)

(73) Assignee: TherOx, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/382,238

(22) Filed: May 8, 2006

(65) Prior Publication Data

US 2006/0193878 A1    Aug. 31, 2006

Related U.S. Application Data

(62) Division of application No. 10/253,572, filed on Sep. 24, 2002, now Pat. No. 7,357,937.

(51) Int. Cl.
*A61K 9/107* (2006.01)
*A61K 9/127* (2006.01)

(52) U.S. Cl. ............... 424/400; 514/832; 514/937; 424/450

(58) Field of Classification Search ............ 424/400, 424/450; 514/832, 937
See application file for complete search history.

(56) References Cited

U.S. PATENT DOCUMENTS 3,778,381 A    12/1973    Rosano et al. ............ 252/311

(Continued)

FOREIGN PATENT DOCUMENTS

DE    4221268 A    1/1994

(Continued)

OTHER PUBLICATIONS

Oxynoid et al. Application of fluorcarbon emulsions as components of cosmetic and medical ointments. Art. Cells, Blood Subs., and Immob. Biotech. 1994; 22(4), 1331-1336.

(Continued)

*Primary Examiner*—Gollamudi Kishore
(74) *Attorney, Agent, or Firm*—Margaret A. Kivinski, PE, Esq.

(57) ABSTRACT

The present invention provides a method of making a FC emulsion. The method comprises mixing an FC immiscible hydrophilic liquid and a solid emulsifying agent by agitation at a temperature elevated above the phase transition temperature of the emulsifying agent and below the boiling temperature of the FC immiscible hydrophilic liquid, and adding FC to the mixture of step (a) and agitating at the elevated temperature to disperse droplets of FC in the FC immiscible hydrophilic liquid to form the FC emulsion. The invention also provides another method of making an FC emulsion, which does not require a solid emulsifying agent. The method comprises mixing an FC immiscible hydrophilic liquid and an emulsifying agent to form a first mixture; mixing a stabilizing agent with the first mixture to form a second mixture; and mixing FC with the second mixture to form a third mixture to disperse droplets of FC in the FC immiscible hydrophilic liquid and to form the FC emulsion, wherein the stabilizing agent reduces ability of the droplets to move within a continuous phase of the FC emulsion.

5 Claims, 3 Drawing Sheets

U.S. PATENT DOCUMENTS

| | | | |
|---|---|---|---|
| 3,932,614 A | 1/1976 | Scott | 424/78 |
| 3,958,014 A | 5/1976 | Watanabe et al. | 424/366 |
| 4,151,108 A | 4/1979 | Sorensen et al. | 252/408 |
| 4,252,827 A | 2/1981 | Yokoyama et al. | 424/366 |
| 4,323,563 A | 4/1982 | Takami et al. | 424/199 |
| 4,366,169 A | 12/1982 | White | 424/285 |
| 4,569,784 A | 2/1986 | Moore | 252/315.1 |
| 4,722,904 A | 2/1988 | Feil | 436/11 |
| 4,758,431 A | 7/1988 | Osterholm | 424/149 |
| 4,865,836 A | 9/1989 | Long, Jr. | 424/5 |
| 4,879,062 A | 11/1989 | Moore | 252/315.1 |
| 4,927,623 A | 5/1990 | Long, Jr. | 424/5 |
| 5,573,757 A | 11/1996 | Reiss et al. | 424/78.02 |
| 5,573,759 A | 11/1996 | Blank | 424/60 |
| 5,576,064 A | 11/1996 | Fructus | 424/401 |
| 5,637,318 A | 6/1997 | Gross et al. | 424/450 |
| 5,643,601 A | 7/1997 | Gross et al. | 424/450 |
| 5,667,772 A * | 9/1997 | Zastrow et al. | 424/78.02 |
| 5,684,050 A | 11/1997 | Clark, Jr. et al. | 514/749 |
| 5,834,519 A | 11/1998 | Spears | 514/938 |
| 5,851,444 A | 12/1998 | Hansell et al. | 261/106 |
| 5,851,544 A | 12/1998 | Penska et al. | 424/401 |
| 5,885,564 A | 3/1999 | Zastrow et al. | 424/74 |
| 5,922,305 A | 7/1999 | Spears | 424/43 |
| 5,925,364 A | 7/1999 | Ribier et al. | 424/401 |
| 5,958,377 A | 9/1999 | Spears | 424/43 |
| 6,066,328 A | 5/2000 | Ribier et al. | 424/401 |
| 6,113,919 A | 9/2000 | Reiss et al. | 424/400 |
| 6,169,117 B1 | 1/2001 | Spears | 514/937 |
| 6,197,279 B1 | 3/2001 | Spears | 424/43 |
| 6,228,378 B1 | 5/2001 | Takanabe et al. | 424/401 |
| 6,238,645 B1 | 5/2001 | Spears | 424/43 |
| 6,262,126 B1 | 7/2001 | Meinert | 514/746 |
| 2002/0102216 A1 | 8/2002 | Lanza et al. | 424/9.52 |
| 2002/0164379 A1 * | 11/2002 | Nishihara et al. | 424/600 |

FOREIGN PATENT DOCUMENTS

| | | |
|---|---|---|
| GB | 1549038 | 7/1979 |
| WO | WO 96/40057 | 12/1996 |

OTHER PUBLICATIONS

Creech et al., Method of Making Perfluorocarbon Emnulsions with Non-Fluorinated Surfactants, U.S. Appl. No. 11/382,234, Confirmation No. 5737, filed May 8, 2006.

* cited by examiner

METHOD OF PREPARING GAS DELIVERING PERFLUOROCARBON EMULSIONS WITH NON-FLUORINATED SURFACTANTS

CROSS-REFERENCE TO THE RELATED APPLICATIONS

This application is a divisional of U.S. patent application Ser. No. 10/253,572, filed Sep. 24, 2002, which is incorporated herein by reference.

FIELD OF THE INVENTION

The invention relates generally to stable emulsions capable of gas-supersaturation, and methods of their preparation and use. Specifically, the present invention relates to stable fluorocarbon emulsions prepared with non-fluorinated emulsifying and stabilizing agents and methods of their preparation utilizing conventional mixing equipment.

BACKGROUND OF THE INVENTION

Fluorocarbons (fluorine substituted hydrocarbons) and perfluorocarbons (fluorocarbons in which all of the hydrogen atoms have been replaced with fluorine) have numerous applications in the biomedical field because of their unique chemical and biological properties. These compounds are clear, colorless, odorless, nonflammable, biocompatible, and have low reactivity. In addition, they are capable of having dissolved in them large amounts of gases, including oxygen, carbon dioxide, and air, per unit volume (WO 96/40057). Accordingly, fluorocarbons (FCs) and perfluorocarbons (PFCs) have been successfully used as carriers in applications wherein oxygen must be supplied to organs and tissues.

For example, it has been demonstrated that liquid ventilation with PFCs quickly and efficiently returns arterial oxygen and carbon dioxide blood gas pressures to normal physiological values in premature lambs suffering from respiratory distress syndrome (H.-J. Lehmler et al., *Chemtech*, 1999, v. 29, No.10, 7-12). Aqueous emulsions of PFCs have been explored as artificial blood substitutes or as perfusion fluids for the preservation of internal organs to be transplanted (GB 1,549,038). Some FC blood substitutes, such as FLUOSOL® (Green Cross Corporation, Osaka, Japan) and OXYGENT® (Alliance Pharmaceutical Corp., San Diego, Calif.) have been clinically evaluated. A synthetic cerebrospinal fluid comprising an oxygenated FC emulsion has been used to deliver oxygen to ischemic neurologic tissue (U.S. Pat. No. 4,758, 431).

Compositions of FCs may also be used for the treatment of wounds, for example, burns, as described in U.S. Pat. No. 4,366,169. The patent teaches contacting a wound with a liquid fluorocarbon directly, or indirectly through a dressing, such as a sponge, gauze, foam, dispersion or gel. Recently, the application of FC emulsions in cosmetics and dermatology has been suggested. It is believed that by delivering oxygen into the skin, FC emulsions may improve skin metabolism, impede skin aging, and protect skin from injurious environmental effects (Oxynoid, O. E. et al., *Art. Cells, Blood Subs., and Immob. Biotech.*, 1994, 22(4), 1331-1336).

Fluorocarbons are extremely hydrophobic and are not miscible with most organic or aqueous systems. Therefore, typically, FCs and PFCs are used in the forms of aqueous emulsions, dispersions, and gels. The stability of the FC emulsions, dispersions, and gels is a key concern in their biomedical use (U.S. Pat. No. 6,113,919).

The dispersed phase of fluorocarbon emulsions must have a stable particle size to be suitable for biomedical use. One of the shortcomings of existing emulsions is their low stability. The particle size of a commercially available fluorocarbon emulsion, such as FLUOSOL, for example, can be maintained only if it is transported and stored in a frozen state. The frozen emulsion is then defrosted and mixed with annex solutions before use. These storage requirements seriously limit the field of application of such fluorocarbon emulsions. Although more stable fluorocarbon emulsions are being developed, it is desirable to have fluorocarbon emulsions that are stable enough to store for long periods without refrigeration and in various packaging configurations for such applications, such as topical, spray, ointment, etc.

Fluorocarbons are oily substances that are immiscible with water, and therefore, fluorocarbon-in-water emulsions are generally prepared by using emulsifying agents, such as lecithins and/or poloxamers, such as Pluronic-F-68, to disperse the fluorocarbon and stabilize the emulsion. However, most conventional emulsifying agents have a low affinity for fluorocarbons.

Several strategies in preparing stable FC emulsions have been explored by researchers. One approach involves dispersing very small FC droplets, less than 0.3 μm, preferably 20-200 nm in diameter, in a continuous phase. This approach is particularly advantageous in blood substitute applications because emulsions with larger droplet sizes can be dangerous in intravenous use (GB 1,549,038; U.S. Pat. No. 4,865,836). However, since the gas dissolved in a larger droplet may be released over a more extended period of time, stable emulsions comprising larger FC droplets are desirable to achieve a maximum therapeutic effect in topical applications.

A surfactant (or emulsifying agent) may be used to stabilize the dispersed droplets through the electrostatic and steric repulsion of the surfactant molecules that surround each dispersed PFC or FC droplet. For example, U.S. Pat. Nos. 4,569, 784 and 4,879,062 describe a stable gel of FC comprising up to 10% (wt/wt) emulsifier. The FC gel is prepared by a multi-step procedure comprising preparing an FC emulsion, concentrating the FC emulsion by a high-speed centrifugation, and removing excess fluid by a separation process. In this method, the type and the quantity of the surfactant used is not crucial, as long as it provides effective emulsification. However, this method involves a complex multi-step procedure and requires high pressure homogenization or sonically-induced cavitations to effectively disperse fluorocarbons in water.

Another approach to improving the stability of fluorocarbon emulsions is to develop more effective surfactants, for example, those which are fluorophilic. Fluorinated surfactants have been shown to improve the stability of FC emulsions (U.S. Pat. No. 6,113,919) However, this class of surfactants has also been shown to have a negative environmental impact that led to the withdrawal of some previously commercially available fluorinated surfactants.

U.S. Pat. Nos. 5,573,757 and 6,113,919 focus on the further improvement of the available surfactant systems. A stable FC emulsion is prepared by utilizing a combination of a surfactant and a fluorophilic/lipophylic compound, which act together in association to stabilize the emulsion by surrounding the dispersed droplets and preventing their coalescence. However, the environmental concerns associated with such fluorinated compounds have greatly limited their use and availability in recent years.

Another strategy is to prepare microemulsions, i.e., preparations of compounds which organize themselves spontaneously into dispersed systems (U.S. Pat. No. 3,778,381; FR A 2 515 198). Microemulsions, while stable thermodynamically, require a substantial amount of surfactants in their formulations, which may lead to bioincompatibiltiy for medical applications. In an example of a microemulsion described by Cecutti et al., Eur. J. Med. Chem., 24, 485-492 (1989), the dispersed phase is itself totally constituted of mixed hydrocarbon/fluorocarbon molecules. Thermodynamically stable microemulsions, when broken, can be restored by a mild agitation. U.S. Pat. No. 4,722,904 teaches a PFC microemulsion comprising a system of two surfactants, the primary surfactant being non-ionic and water-soluble, and the secondary surfactant being hydrotropic and present in an amount sufficient to disorder any water-primary surfactant gels. However, it is not clear whether such microemulsions are suitable for biomedical and cosmetic applications. So far, PFC microemulsions have been used only as reference liquid for the calibration and/or quality control of blood gas analyzers (U.S. Pat. Nos. 4,151,108 and 4,722,904) and their safety for intravenous use has been questioned (U.S. Pat. No. 6,113,919).

U.S. Pat. No. 5,637,318 describes a dermatological agent containing an emulsion of asymmetrical lamellar aggregates comprising FC surrounded by at least three layers of phospholipid molecules. The dermatological agent is prepared using an ultrasonic disintegrator and the stability of the emulsion is achieved by limiting the size of the lamellar aggregates to 50-1000 nm, with a mean diameter of 244 nm.

Therefore, a number of conventional FC emulsions, dispersions, and gels are prepared by multi-step complex methods that utilize a high-pressure apparatus or ultrasound to form an emulsion and require further concentration by centrifugation. Other FC emulsions are stabilized with fluorinated surfactants that cause certain environmental concerns or by forming microemulsions that have not been used in biomedical applications to date. Still another group of FC emulsions limit the size of the FC droplets and do not provide an optimal therapeutic effect in topical applications.

SUMMARY OF THE INVENTION

In view of the above-noted shortcomings of the conventional FC emulsions and methods of their preparation, it is an object of the present invention to provide stable FC emulsions using non-fluorinated emulsifying agents. It is also an object of the present invention to provide simple and low energy methods for preparing stable FC emulsions and gels by utilizing conventional mixing equipment. It is a further object of the present invention to provide methods that allow the preparation of stable FC emulsions with a broad range of FC droplet sizes.

These and other objects are achieved in the present invention by using a stabilizing agent that reduces the ability of the FC droplets to move within the continuous phase. Conventionally, the FC emulsions are stabilized either by decreasing the size of the dispersed FC droplets and/or by selecting a surfactant that surrounds the fluorocarbon droplets reducing interfacial surface tension and causing electrostatic and steric repulsion between the droplets, inhibiting their coalescence. The present invention, on the other hand, stabilizes the FC emulsion by further decreasing the ability of the dispersed FC droplets to move within the continuous phase. This result is achieved by several means including using a stabilizing agent to alter the physical properties of the continuous phase, an emulsifying agent, and a method of making the emulsion that result in a highly stabilized fluorocarbon emulsion.

Accordingly, one aspect of the present invention is directed to a fluorocarbon (FC) emulsion, comprising:

a continuous FC immiscible hydrophilic liquid phase; and a dispersed phase comprising FC suspended as droplets within the continuous phase;

the emulsion further comprising an emulsifying agent and a stabilizing agent, wherein the stabilizing agent reduces the ability of the FC droplets to move within the continuous phase.

The FC may be selected from the group consisting of linear, branched and cyclic fluorinated hydrocarbon compounds, derivatives and mixtures thereof. The FC may be a PFC. In one embodiment, the PFC is perfluorodecalin. The PFC may also be substituted, such as with bromine or iodine. If substituted, the perfluorocarbon may be perfluorooctyl bromide or perfluorooctyl iodine.

The stabilizing agent may be selected from a group consisting of cetyl alcohol, stearyl alcohol, behenyl alcohol, glyceryl stearate, polyoxyethylated fatty acid (PEG-75 stearate), polyethylene glycol ether of cetyl alcohol (ceteth-20), polyethylene glycol ether of stearyl alcohol (steareth-20), hydrogenated phosphotidylcholine, and mixtures thereof. The amount of the stabilizing agent may be in the range from about 0.05% to about 10% (wt/wt). In another embodiment, both the stabilizing agent and the emulsifying agent are hydrogenated phosphotidyl choline.

The continuous FC immiscible hydrophilic liquid phase of the present invention may further comprise a thickening agent to increase the viscosity of the emulsion. In one embodiment, the thickening agent is selected from the group consisting of carboxylic acid polymers, polyacrylamide, polysaccharides, and gums.

Another aspect of the present invention is directed to a method of making an FC emulsion. The method comprises:

(a) mixing an FC immiscible hydrophilic liquid and a solid emulsifying agent by agitation at a temperature elevated above the phase transition temperature of the emulsifying agent and below the boiling temperature of the FC immiscible hydrophilic liquid; and (b) adding FC to the mixture of step (a) and agitating at the elevated temperature to disperse droplets of FC in the FC immiscible hydrophilic liquid and to form the FC emulsion.

The FC immiscible hydrophilic liquid of the present invention can be glycerin, an aqueous solution or other liquid that is hydrophilic and not miscible with the FC. The aqueous solution is water or a solution comprising water and components soluble or dispersable in water, including stabilizing agents, humectants or other additives that may provide desirable characteristics to the finished emulsion.

Preferably, the emulsifying agent is a non-fluorinated compound. In one embodiment, the non-fluorinated emulsifying agent is a hydrogenated phospholipid. The hydrogenated phospholipid may be selected from the group consisting of hydrogenated phosphatidylcholine, lysophosphatidylcholine, phosphatidylethanolamine, phosphatidylserine, phosphatidylinositol, phosphanolipids, phosphatidic acid, and mixtures thereof.

The elevated temperature is in the range from about 40° C. to about 90° C. The above-described method may further comprise a step of cooling the obtained emulsion to form a viscous solution or gel.

The instant invention also provides another method of making an FC emulsion, which does not require a solid emulsifying agent. The method comprises:

(a) mixing an FC immiscible hydrophilic liquid and an emulsifying agent to form a first mixture;

(b) mixing a stabilizing agent with the first mixture to form a second mixture; and (c) mixing FC with the second mixture to form a third mixture to disperse droplets of FC in the FC immiscible hydrophilic liquid and to form the FC emulsion, wherein the stabilizing agent reduces the ability of the droplets to move within a continuous phase of the FC emulsion.

A further aspect of the present invention is directed to an oxygen delivery agent for the delivery of oxygen into oxygen-depleted environments. The agent comprises the FC emulsion described above, wherein the FC emulsion is saturated or supersaturated with oxygen. In one embodiment, the oxygen delivery agent contains at least about one ml of oxygen at standard temperature and pressure (STP) per one ml of FC emulsion.

The present invention also provides a method of preparing an oxygen delivery agent. The method comprises:

(a) providing the FC emulsion described above; and (b) exposing the FC emulsion to oxygen under conditions sufficient to oxygenate the emulsion to a predetermined degree.

The emulsion may be oxygenated by exposing it to oxygen gas under atmospheric pressure or under high-pressure (above atmospheric pressure) conditions. In one embodiment, an oxygenated emulsion with a $pO_2$ of up to 10,000 mm Hg may be obtained by exposing the emulsion to oxygen gas at 180 psig for one hour.

The present invention offers many economical and technical advantages over the conventional methods. The present invention provides stable FC emulsions, dispersions, and gels of varying FC contents and drop sizes using non-fluorinated emulsifying agents and conventional mixing equipment. The visco-elastic properties of the FC preparations of the present invention range from low viscosity emulsions/dispersions to highly visco-elastic and semi-solid gels. Also, the FC emulsions of the present invention are capable of dissolving large quantities of gases, such as oxygen and carbon dioxide. Finally, the disclosed methods of preparing FC emulsions involve conventional mixing and do not require further concentrating steps. Accordingly, the methods of the present invention are fast, simple, and inexpensive. Since only standard laboratory equipment is utilized, no specialized training of laboratory personnel is required.

Oxygenated emulsions of the present invention are well-suited to be used in applications in which local delivery of oxygen are desirable. For example, they may be used in topical applications for the healing of wounds, burns, and bruises. The oxygenated emulsions may also be incorporated into pharmaceutical products containing antibiotics, nutritive elements, hydrating agents, and other beneficial and therapeutic substances, for optimal therapeutic and healing effect. In addition, the oxygenated emulsions of the present invention may be incorporated into various cosmetic products, such as creams, ointments, masks, and exfoliates, to name a few.

The above-mentioned and other features of this invention and the manner of obtaining them will become more apparent, and will be best understood, by reference to the following description, taken in conjunction with the accompanying drawings. These drawings depict only a typical embodiment of the invention and do not therefore limit its scope.

DETAILED DESCRIPTION OF THE INVENTION

For the purposes of the present invention, the following terms are defined as follows:

Fluorocarbon is a fluorinated hydrocarbon in which at least one hydrogen atom is replaced by a fluorine atom.

Perfluorocarbon—a substantially fluorinated or completely fluorinated material which is generally, but not necessarily, a liquid at ambient temperature and pressure and which has the ability to transport gases, such as oxygen and carbon dioxide. "Substantially fluorinated" in this specification means that most of the hydrogen atoms of a compound have been replaced by fluorine atoms, such that further replacement does not substantially increase the gas transport capability of the material. It is believed that this level is reached when at least about 80-90% of the hydrogen atoms have been replaced by fluorine atoms (U.S. Pat. No. 4,569,784).

Emulsion—a system consisting of a liquid dispersed with or without an emulsifier in an immiscible liquid in a form of stable (non-coalescing) droplets or microdroplets.

Continuous phase—the carrier phase of an emulsion, wherein the fluid elements are in continuous contact and not isolated from one another.

Dispersed phase—the phase of an emulsion, wherein the fluid elements are discrete and isolated from one another, as in the form of droplets or microdroplets, or contained within micelles.

Thickening agent—a chemical agent having the property that, when added to a liquid mixture, increases its viscosity, or resistance to flow.

Viscous solution—a solution with viscosity greater than about 50 cp, and which may or may not be dependent upon applied shear and/or temperature.

Gel—a semisolid that behaves like a solid at rest. Gels may flow at higher shear rates due to their shear thinning properties. The viscosity of gels may range from a thickened pourable liquid gel to a soft solid stick.

Liquid Crystals—orderly planes of oil and water separated by layers of surfactant. Under certain conditions, a combination of oil, water and surfactant will, instead of forming micelles, result in the formation of such liquid crystals. The liquid crystals may co-exist with regular emulsions. The presence of liquid crystals enhances the stability of the emulsion due to the formation of a covering "skin" around the droplets and also due to the formation of a three-dimensional network through the continuous phase. The covering "skin" prevents the coalescence of droplets. A layered structure also reduces the van der Waals attraction between the droplets, inhibiting coalescence. The three-dimensional network reduces the ability of the droplets to move within the continuous phase (for more information, please refer to "Liquid Crystals and Emulsions" in *Emulsions and Solubilization,* Shinoda K and Friberg S, John Wiley & Sons, Inc. (1986) and Jansson, P. and Friberg, S.; *Molecular Crystals and Liquid Crystals,* 34:75 (1976)).

In its first aspect, this invention provides an FC emulsion, comprising:

a continuous FC immiscible hydrophilic liquid phase; and a dispersed phase comprising FC suspended as droplets within the continuous phase;

the emulsion further comprising an emulsifying agent and a stabilizing agent, wherein the stabilizing agent reduces the ability of the FC droplets to move or coalesce within the continuous phase.

The continuous FC immiscible hydrophilic liquid phase of the FC emulsion of the present invention may include an aqueous phase and other water-miscible substances, such as glycerin, propylene glycol, short-chain alcohols, and other hydrophilic liquids. Such hydrophilic liquids mix readily with water and may be added individually or in combination to the continuous phase.

The water-immiscible dispersed phase of the FC emulsion consists of FCs or derivatives thereof. FCs are chosen for their inert chemistry and high oxygen solubility (about twenty times greater than that of water). Substantially, any FC may be used. Suitable FCs include, but are not limited to, linear, branched and cyclic fluorinated hydrocarbon compounds, derivatives and mixtures thereof. In one embodiment, FC may be a perfluorocarbon (PFC). Examples of acceptable PFCs include, but are not limited to, C6-C9 perfluoroalkanes, perfluoroperhydrofluoranthrene, perfluorodecalin, perfluoroperhydrophenanthrene, bis(perfluor-hexyl)-1,2-ethene, perfluoro-1,3-dimethylcyclohexane, perfluoromethyldecalin, perfluoroisopropyldecalin, a mixture of perfluorodixylylmethane and perfluorodixylylethane, and a mixture of perfluoroperhydrophenanthrene and perfluoro n-butyl decalin.

Hydrogen atoms of the FC may be substituted with a halogen, such as Br, Cl, or I, in addition to fluorine. In one embodiment, the PFC is perfluorooctyl bromide or perfluorooctyl iodine. In another embodiment, a commercial product PFC 5080 (a product of 3M, St. Paul, Minn.) is used. PFC 5080 is a mixture of perfluorocarbons containing predominately perfluorooctane.

The FC emulsions of the present invention may contain FCs in the amount from about 2% to about 90% (wt/wt), preferably from about 10% to about 70% (wt/wt). However, FC concentrations outside of the above ranges may also be used.

Because FCs are oily compounds that are immiscible with water, an emulsifying agent is typically used to prepare an FC-in-water emulsion. The emulsifying agent assists in dispersing FC and stabilizing the emulsion. Any emulsifying agents capable of dispersing FC may be used. However, due to environmental concerns, preferably, the emulsifying agent is a non-fluorinated compound. In biomedical and cosmetic applications, additionally, the emulsifying agent is preferably biocompatible (non-irritating) and should result in an emulsion have a sufficient shelf life. A shelf life of at least six months, preferably greater than one year, is generally considered sufficient.

Examples of such biocompatible, non-fluorinated compounds include, but are not limited to, a block copolymer of ethylene oxide and propylene oxide, phospholipids, and a polyoxyethylene derivative of a fatty acid ester of sorbitan. In one embodiment, the block copolymer of ethylene oxide and propylene oxide is a triblock copolymer of ethylene and propylene oxide with an average molecular weight of 7680 to 9510 and 81 wt % oxyethylene (poloxamer 188) or PLURONIC® F-68 (BASF Corporation, Mount Olive, N.J.). In another embodiment, the emulsifying agent is polyoxyethylene 20 sorbitan monostearate (polysorbate 60).

In still another embodiment, a hydrogenated phospholipid is used. The hydrogenated phospholipid may be selected from the group consisting of hydrogenated phosphatidylcholine, lysophosphatidylcholine, phosphatidylethanolamine, phosphatidylserine, phosphatidylinositol, phosphanolipids, phosphatidic acid, and mixtures thereof. It is anticipated that other emulsifying agents having a hydrophilic-lipophilic balance (HLB) or a combined HLB value similar to that of polysorbate 60 and PLURONIC® F-68 may be used in the preparation of the FC emulsion of the present invention. In a preferred embodiment, the hydrogenated phospholipid is hydrogenated phosphatidylcholine.

Typically, the emulsifying agent is used in an amount in the range from about 1% to about 15% (wt/wt). In one embodiment, the amount of the emulsifying agent is in the range from about 3% to about 7% (wt/wt). However, greater amounts may be used if desired.

As explained in the Introduction section, conventional FC emulsions are stabilized either by decreasing the size of the dispersed FC droplets and/or by selecting a surfactant that surrounds the fluorocarbon droplets and reduces the interfacial surface tension and causing electrostatic and steric repulsion between the droplets, inhibiting their coalescence.

Surfactants are commonly amphiphilic molecules having a hydrophobic tail region and hydrophilic head region. However, FCs are water-immiscible substances that are neither hydrophilic nor lipophilic. Thus, the interfacial surface tension between FCs and an FC immiscible hydrophilic liquid phase cannot be effectively reduced by conventional surfactants alone. Accordingly, U.S. Pat. No. 6,113,919 teaches the use of a combination of a conventional surfactant and a fluorophilic/lipophilic molecule, which act together in association to reduce the interfacial surface tension and stabilize the emulsion.

This invention takes a different approach that does not require the use of fluorophilic/lipophilic compounds. Instead, in this invention, the FC emulsion is unexpectedly stabilized by decreasing the ability of the dispersed FC droplets and micelles to move within the continuous phase altogether. As a result, the FC droplets cannot combine with each other and destabilize the emulsion. It is a discovery of the present invention that the mobility of FC droplets may be decreased by adding a stabilizing agent to the continuous phase to alter the physical properties of that phase.

Accordingly, the stabilizing agent of the present invention is a compound that reduces the ability of the FC droplets to move within the continuous phase. The stabilizing agent may be selected from the group consisting of cetyl alcohol, stearyl alcohol, behenyl alcohol, glyceryl stearate, polyoxyethylated fatty acid (PEG-75 stearate), polyethylene glycol ether of cetyl alcohol (ceteth-20), polyethylene glycol ether of stearyl alcohol (steareth-20), hydrogenated phosphotidylcholine, and mixtures thereof.

Typically, the amount of the stabilizing agent is in the range from about 0.05% to about 20% (wt/wt). Preferably, the amount of the stabilizing agent is in the range from about 0.5% to about 5% (wt/wt).

In one embodiment, hydrogenated phosphotidyl choline is used as both the stabilizing agent and the emulsifying agent.

The FC emulsion of the present invention may be in a form of a viscous solution, liquid crystal, or gel. In one embodiment, the continuous aqueous phase further comprises a thickening agent to increase the viscosity of the emulsion. Preferably, the thickening agent is added in such an amount that the viscosity of the FC emulsion is at least about 50 centipoise under normal conditions.

The thickening agent may be selected from the group consisting of the FC emulsion of claim 24, wherein the thickening agent is selected from the group consisting of carboxylic acid polymers, polyacrylamide, polysaccharides, and gums. The carboxylic acid polymers may be homopolymers of acrylic acid cross-linked with allyl ethers of sucrose or pentaerytritol (carbomers) or copolymers of C10-30 alkyl acrylates with one or more monomers of acrylic acid or methacrylic acid cross-linked with allyl ethers of sucrose or pentaerytritol (acrylates/C10-30 alkyl acrylate crosspolymers).

The polysaccharides may be cellulose and cellulose derivatives. In one embodiment, the polysaccharides are selected from the group consisting of hydroxyethyl cellulose, carboxymethyl hydroxyethyl cellulose, microcrystalline cellulose, cetyl hydroxyethyl cellulose, hyaluronic acid, chitosan, dextran, and derivatives thereof.

The gums may be selected from the group consisting of agars, gelatin, guar gum, and algin.

As explained above, it is an unexpected discovery of the present invention that the mobility of the FC particles within the continuous phase may be decreased and the FC emulsion may be stabilized by adding a stabilizing agent to the continuous phase. Accordingly, another aspect of the present invention is directed to methods of making an FC emulsion. The method comprises:

(a) mixing an FC immiscible hydrophilic liquid and an emulsifying agent to form a first mixture;

(b) mixing a stabilizing agent with the first mixture to form a second mixture; and (c) mixing FC with the second mixture to form a third mixture to disperse droplets of FC in the FC immiscible hydrophilic liquid and to form the FC emulsion, wherein the stabilizing agent reduces the ability of the droplets to move within a continuous phase of the FC emulsion.

It is also an unexpected discovery of the present invention that mechanical agitation of the heated ingredients, including a solid emulsifying agent, forms a stable suspension of FC droplets within the continuous phase. The FC emulsion obtained in accordance with the above method is thermally and mechanically stable and will not separate into its constituent phases unless subjected to extreme conditions.

Accordingly, the present invention also provides another method of making an FC emulsion. This method comprises:

(a) mixing an FC immiscible hydrophilic liquid and a solid emulsifying agent by agitation at a temperature elevated above the phase transition temperature of the emulsifying agent and below the boiling temperature of the FC immiscible hydrophilic liquid; and (b) adding FC to the mixture of step (a) and agitating at the elevated temperature to disperse droplets of FC in the FC immiscible hydrophilic liquid and to form the FC emulsion.

The mixing and agitation may be conducted by any conventional means, for example, by hand stirring, aeration, propeller agitation, turbine agitation, colloid milling, homogenizing, high-frequency or ultrasonic oscillation (sonication), micro-fluidization and the like. In one embodiment, a homogenizer is used.

Due to environmental concerns, the emulsifying agent used in either method is preferably a non-fluorinated compound. The emulsifying agent may be selected from the group consisting of a block copolymer of ethylene oxide and propylene oxide, phospholipids, and a polyoxyethylene derivative of a fatty acid ester of sorbitan. In one embodiment, the block copolymer of ethylene oxide and propylene oxide is a triblock copolymer of ethylene and propylene oxide with an average molecular weight of 7680 to 9510 and 81 wt % oxyethylene (poloxamer 188 or PLURONIC® F-68). In another embodiment, the emulsifying agent is polyoxyethylene 20 sorbitan monostearate (polysorbate 60).

When a solid emulsifying agent is required, it is preferably a hydrogenated phospholipid. The hydrogenated phospholipid may be selected from the group consisting of hydrogenated phosphatidylcholine, lysophosphatidylcholine, phosphatidylethanolamine, phosphatidylserine, phosphatidylinositol, phosphanolipids, phosphatidic acid, and mixtures thereof. In one embodiment, the hydrogenated phospholipid is a hydrogenated phosphotidyl choline.

Typically, the amount of the emulsifying agent is in the range from about 1% to about 15% (wt/wt), preferably, in the range from about 3% to about 7% (wt/wt).

Typically, the elevated temperature is in the range from about 40° C. to about 90° C.

This method may further comprise a step of cooling the obtained emulsion to form a viscous solution or gel. In one embodiment, the viscosity of the viscous solution is greater than the viscosities of plasma and blood, which are in the range of 1 to 6 centipoise. In another embodiment, the viscosity is at least about 50 centipoise.

In one embodiment, the FC emulsion is cooled to at least about 40° C.

The above-described method of making FC emulsion may further comprise a step of processing the viscous solution to reduce the size of the FC droplets. Such processing step may be conducted by homogenization or other suitable methods known to those skilled in the art.

Depending on the type of the intended use of the FC emulsion of the present invention, step (a) of the above method may further comprise admixing formulation additives into water. Such formulation additives are well known to those skilled in the art and may be selected from a group consisting of stabilizing agents, thickening agents, preservatives, humectants, emollients, colorants, pH adjustment agents, buffers, texture-enhancing compounds, sunscreens, antioxidants, chelating agents, fragrances, flavorings, processing aids, and other bioactive or inert cosmetic and pharmaceutical ingredients.

For example, the stabilizing agent may be selected from a group consisting of cetyl alcohol, stearyl alcohol, behenyl alcohol, glyceryl stearate, polyoxyethylated fatty acid (PEG-75 stearate), polyethylene glycol ether of cetyl alcohol (ceteth-20), polyethylene glycol ether of stearyl alcohol (steareth-20), hydrogenated phosphotidylcholine, and mixtures thereof. The amount of the stabilizing agent may be in the range from about 0.05% to about 20% (wt/wt), preferably, from about 0.5% to about 5% (wt/wt). In one embodiment, both the stabilizing agent and the emulsifying agent are hydrogenated phosphotidyl choline. The humectants are substances that are added into formulations to preserve the moisture content of the materials to which they are added, slow evaporation and enhance moisturization. The humectants are well known in the art and may be selected from the group consisting of glycerin, propylene glycol, butylene glycol, sorbitol and others. Other additives are also well known in the art and may be may be selected from the group consisting of thixotropic, whitening agents and processing aids. Thixotropic agents are added generally to alter the flow characteristics, or rheology, of the emulsion.

In another aspect of the present invention, the emulsion may be treated to contain more gas, preferably oxygen, than would result under normal conditions. Accordingly, the present invention provides a gas delivery agent for the delivery of gas into gas-depleted environments. The agent comprises the FC emulsion described above, wherein the FC emulsion is saturated with a gas. When the gas is oxygen, the concentration of oxygen in the FC emulsion of the present invention is at least about 0.3 ml of oxygen (STP) per one ml of FC emulsion at 1 atmosphere. The partial pressure of oxygen, or $pO_2$, in the emulsion is generally above 760 mm Hg in these embodiments The gas delivery agent of the present invention may be supersaturated with gas. For example, in one embodiment in which the gas is oxygen, the concentration of oxygen in the emulsion is at least about 1 ml of oxygen (STP) per one ml of FC emulsion. In another embodiment, the concentration of oxygen in the emulsion is at least about 2 ml of oxygen (STP) per ml of FC emulsion. The partial pressure of oxygen, or $pO_2$, in the emulsion is generally above 10,000 mm Hg in these embodiments, and can be as high as 11,000 mm Hg or higher.

The present invention also provides a method of preparing a gas delivery agent. The method comprises:

(a) providing the FC emulsion of the present invention; and
(b) exposing the FC emulsion to a gas under conditions sufficient to gasify the emulsion to a predetermined degree.

The FC emulsion may be exposed to gas under atmospheric pressure or under a pressure that is above atmospheric pressure. For example, when the gas is oxygen, the emulsion may be exposed to oxygen under 180 psi for sufficient time to achieve $pO_2$ in the emulsion of at least about 10,000 mm Hg.

Figure 1:
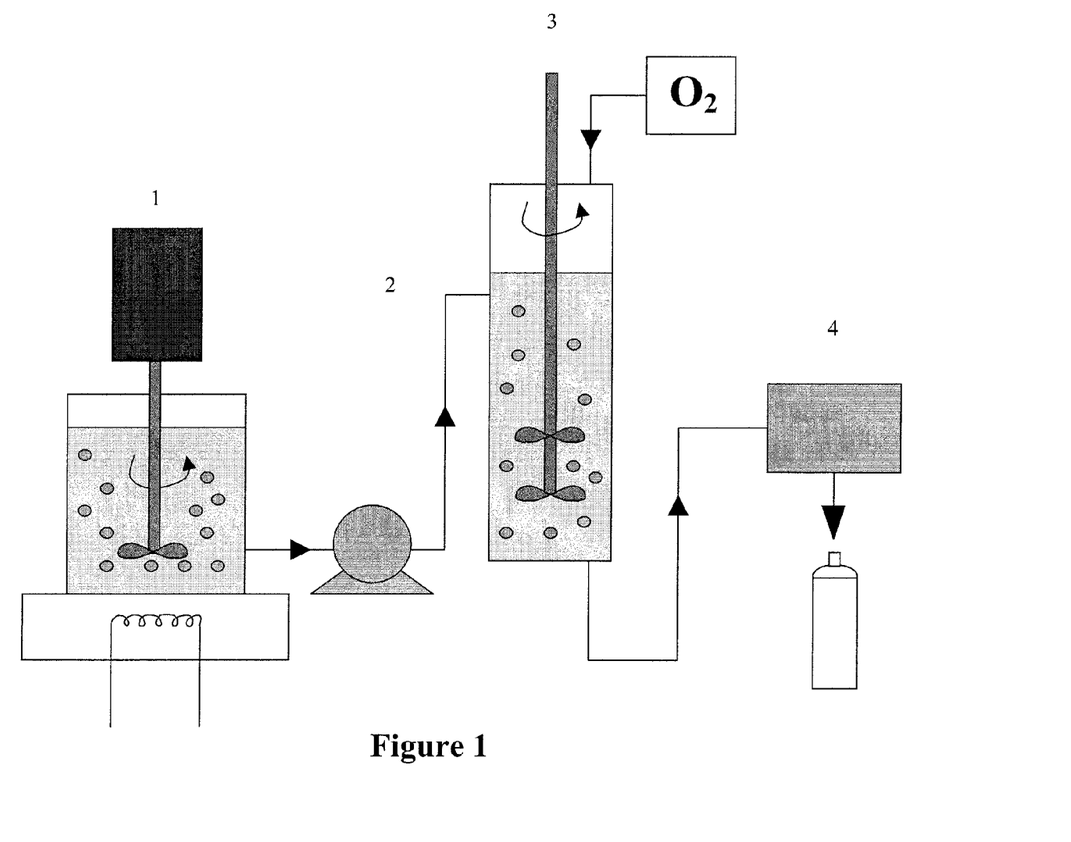
FIG. 1 schematically represents a production process for oxygen delivery agent in accordance with one embodiment of the present invention.

In one embodiment, illustrated in FIG. 1, the ingredients of the FC emulsion are heated and mixed in a mixer 1 and the obtained emulsion is pumped by pump 2 into a pressurized oxygenation vessel 3. Mechanical agitation is performed in this unit with dual pitched blades to ensure rapid equilibration with oxygen to produce an oxygen delivery agent. Lastly, the internal pressure of the oxygenation vessel 3 forces the oxygen delivery agent into the filling station 4 for bottling.

Because the oxygen delivery agent of the present invention is capable of delivering high levels of oxygen into the skin tissues, it has many biomedical and cosmetic applications. For example, it may be used in topical applications for the healing of wounds, burns, and bruises. The oxygen delivery agent may also be incorporated into pharmaceutical products containing antibiotics, nutritive elements, hydrating agents, and other beneficial and therapeutic substances, for optimal therapeutic and healing effect. The oxygen delivery agent may be applied directly to the skin or may be incorporated into a dressing for application to the skin. Examples of such dressings include, but are not limited to, gauze, bandages, and other materials suitable for maintaining the oxygen delivery agent in contact with the skin. Application of an occlusive wound dressing inhibits diffusive transport of oxygen to the ambient environment and ensures maximal transport of oxygen to the treatment site.

The oxygen delivery agent may also be incorporated into various cosmetic products, such as creams, ointments, masks, and exfoliates, to name a few. In one embodiment, the oxygen delivery agent of the present invention delivers oxygen to intact skin in cosmetic applications to improve skin texture and tone. For example, the oxygen delivery agent may be incorporated into a skin care cream or a cosmetic mask. Such products may be applied by a skilled skin care professional in the office or by a consumer at home.

The FC emulsion or gas delivery agent of the present invention is preferably stored under pressure in a dispensing bottle to maintain the phase equilibria between the solubilized gas in the FC emulsion and the pressurized gas and to prevent gas dissolution and escape from the emulsion. When the gas is oxygen, oxygen gas may also serve as the vehicle propellant in such a delivery system, or, an indirect propellant, such as another gas, for example, nitrogen, applied to the outside of a barrier within the dispensing bottle, can be employed.

Preferably, the pressurized container holding the gas delivery agent should maintain an internal pressure that, at a minimum, remains equal to or greater than the equivalent dissolved gas partial pressure. Also, in a preferred embodiment, the pressurized container allows full dispensation of the gas delivery agent (greater than 95% of total charging weight dispensed).

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

EXAMPLES

Example 1

Preparation of the FC emulsion

| | Ingredients | % (wt/wt) |
|---|---|---|
| A | Water | 42 |
| B | Glycerin | 12 |
| C | Hydrogenated Phospholipid | 4.5 |
| D | Cetyl alcohol | 0.6 |
| E | Stearyl alcohol | 0.6 |
| F | Polysorbate 60 | 0.5 |
| G | Perfluorodecalin | 39.5 |
| H | Tocopheryl acetate | 0.4 |

A is mixed into B. The mixture is heated to 70° C. in a reaction vessel with agitation. When the temperature reaches 70° C., C is added to the mixture at 70° C. with agitation. An overhead stirrer is used to conduct this step. After C is uniformly dispersed in the mixture, D, E and F are added with continued agitation. When all of the above ingredients are uniformly dispersed, G is added slowly at a controlled rate with agitation. When all G has been added, H is added while maintaining the temperature at 70° C. The mixture is cooled slowly to room temperature. Alternatively, prior to cooling, the mixture may be subjected to homogenization and then cooled slowly to room temperature.

Example 2

Preparation of alternate FC emulsion

| | Ingredients | % (wt/wt) |
|---|---|---|
| A | Water | 42.5 |
| B | Propylene Glycol | 30 |
| C | Hydrogenated Phospholipid | 4.4 |
| D | Cetyl alcohol | 0.3 |
| E | Stearyl alcohol | 0.3 |
| F | Polysorbate 60 | 0.2 |
| G | Glyceryl stearate, PEG-75 stearate, ceteth-20, steareth-20 (Emulium Delta, Gattefosse, France) | 0.8 |
| H | Perfluorodecalin | 20 |
| I | Tocopheryl acetate | 0.5 |
| J | Dimethicone | 0.7 |
| K | Benzyl alcohol | 0.4 |
| L | Methyl paraben | 0.1 |
| M | Propyl paraben | 0.05 |
| N | Hyaluronic acid | 1 |

A is mixed into B. The mixture is heated to 70° C. in a reaction vessel with agitation. When the temperature reaches 70° C., C is added to the mixture at 70° C. with agitation. An overhead stirrer is used to conduct this step. After C is uniformly dispersed in the mixture, D, E, F and G are added with continued agitation. When all of the above ingredients are uniformly dispersed, H is added slowly at a controlled rate with agitation. When all H has been added, I and J are added while maintaining the temperature at 70° C. The mixture is cooled slowly to room temperature. While the mixture is cooling, K, L, M and N are added. Alternatively, prior to cooling, the mixture may be subjected to homogenization and then cooled slowly to room temperature.

Example 3

Preparation of alternate FC emulsion

|   | Ingredients | % (wt/wt) |
|---|---|---|
| A | Water | 48 |
| B | Propylene Glycol | 34 |
| C | Hydrogenated Phospholipid | 4 |
| D | Cetyl alcohol | 0.4 |
| E | Stearyl alcohol | 0.4 |
| F | Polysorbate 60 | 0.3 |
| G | Glyceryl stearate, PEG-75 stearate, ceteth-20, steareth-20 (Emulium Delta, Gattefosse, France) | 1 |
| H | Perfluorodecalin | 10 |
| I | Tocopheryl acetate | 0.8 |
| J | Dimethicone | 0.5 |
| K | Benzyl alcohol | 0.4 |
| L | Methyl paraben | 0.1 |
| M | Propyl paraben | 0.05 |

A is mixed into B. The mixture is heated to 70° C. in a reaction vessel with agitation. When the temperature reaches 70° C., C is added to the mixture at 70° C. with agitation. An overhead stirrer is used to conduct this step. After C is uniformly dispersed in the mixture, D, E, F and G are added with continued agitation. When all of the above ingredients are uniformly dispersed, H is added slowly at a controlled rate with agitation. When all H has been added, I and J are added while maintaining the temperature at 70° C. The mixture is cooled slowly to room temperature. While the mixture is cooling, K, L and M are added. Alternatively, prior to cooling, the mixture may be subjected to homogenization and then cooled slowly to room temperature.

Example 4

Preparation of the Oxygen Delivery Agent

Figure 2:
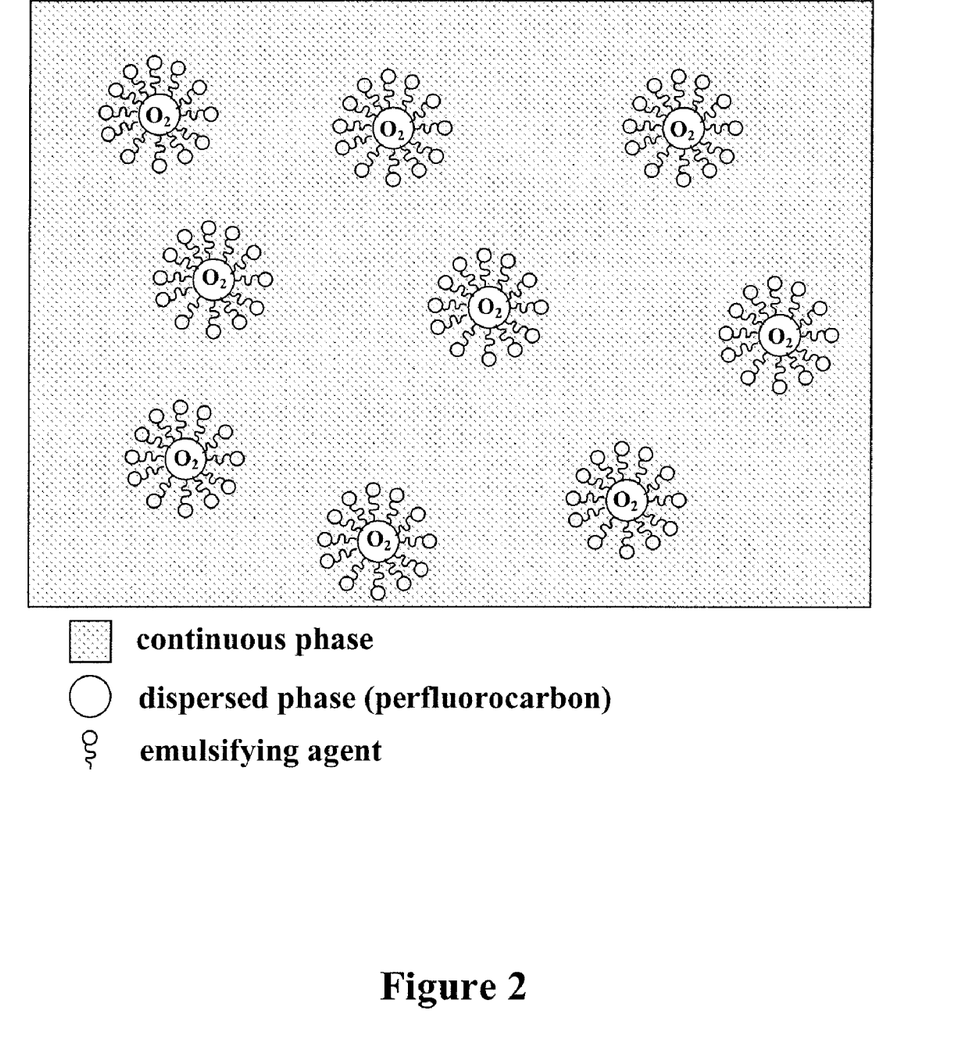
FIG. 2 schematically represents an oxygen delivery agent prepared in accordance with an embodiment the present invention.

The FC emulsion prepared in accordance with any of Examples 1 through 3 is charged with 180 psi of oxygen in a pressurized mixer for 90 minutes. The obtained oxygen delivery agent is packaged in a pressurized canister, containing approximately 1.8 ml of oxygen (STP) per ml FC. A schematic representation of the oxygen delivery agent is shown in FIG. 2.

Example 5

Oxygen Transfer in Freshly Harvested Porcine Skin Tissue

A needle oxygen measuring device ($FO_2TON$ Measuring System, Ocean Optics, Inc.), calibrated for temperature, was used to measure tissue oxygen levels that penetrated approximately 1 mm thick pig skin sections on the bench.

Freshly harvested porcine skin was shaved and cut to a thickness of approximately 1 mm, leaving the epidermis intact. The oxygen delivery agent of Example 2 was applied to the external surface of two skin sections (Sample 1 and Sample 2), while a direct-contact $pO_2$ probe was applied to the opposite side.

Figure 3:
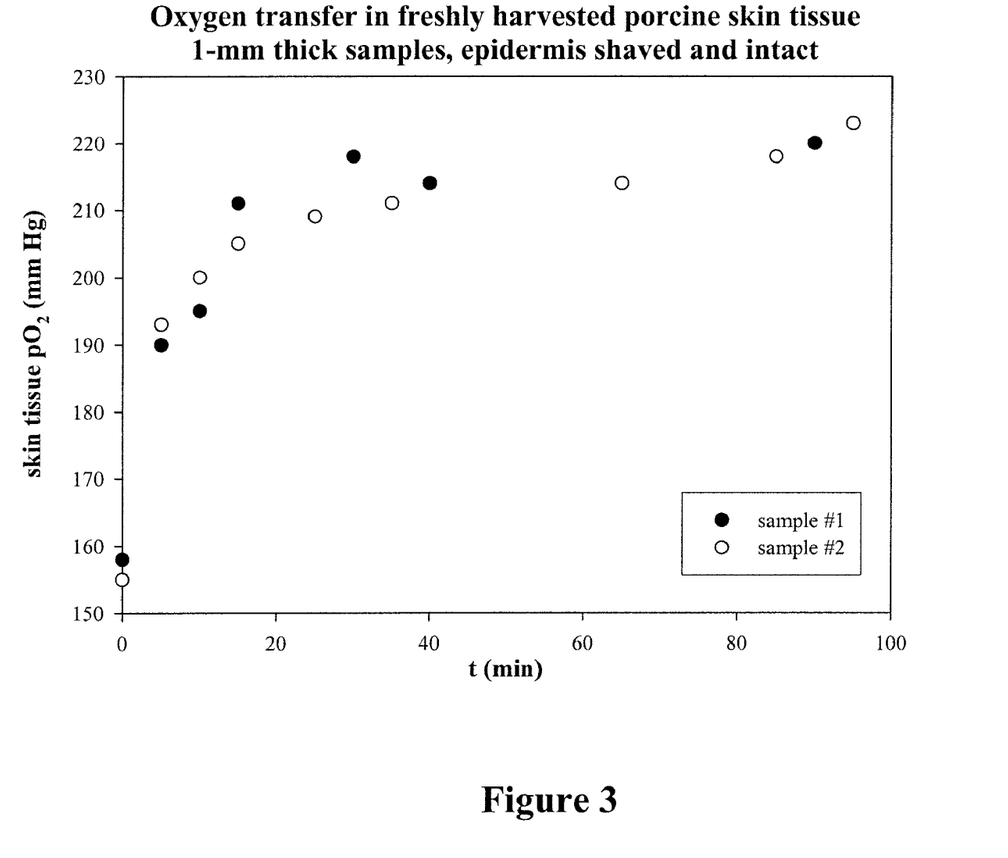
FIG. 3 shows partial oxygen pressure ($pO_2$) of porcine skin as a function of time in an in vitro model.

FIG. 3 shows partial oxygen pressure ($pO_2$) of porcine skin as a function of time over a period of approximately 90 minutes. The continuous measurements showed an elevation of transdermal oxygen levels to approximately 200 mm Hg, with the increase occurring over a 30-minute period and sustained for at least 1 full hour. However, because of the slaughterhouse treatment of the skin (blanching) that generally impedes absorption/convection of oxygen, better oxygen transfer is expected in fresh skin specimens.

The invention claimed is:

1. A method of preparing a gas delivery agent for delivering a gas, the method comprising:
   (a) providing a fluorocarbon (FC) emulsion, comprising:
      (1) a continuous FC immiscible hydrophilic liquid phase; and
      (2) a dispersed phase comprising FC suspended as droplets within the continuous phase;
   the emulsion further comprising an emulsifying agent and a stabilizing agent, wherein the stabilizing agent reduces the ability of the FC droplets to move within the continuous phase; and
   (b) exposing the FC emulsion to the gas under conditions sufficient to gasify the emulsion such that the resulting FC gas content has a concentration of the gas in the emulsion at or above 760 mm Hg.

2. The method of claim 1, wherein said conditions in the exposing step comprises exposing the emulsion to the gas under a pressure that is at atmospheric pressure.

3. The method of claim 1, wherein said conditions in the exposing step comprises exposing the emulsion to the gas under a pressure that is above atmospheric pressure.

4. The method of claim 3, wherein the gas is oxygen and the emulsion is exposed to oxygen under 180 psi.

5. A gas delivery agent prepared in accordance with the method of claim 1.

* * * * *